US011690669B2

(12) United States Patent
Byrd

(10) Patent No.: US 11,690,669 B2
(45) Date of Patent: Jul. 4, 2023

(54) ELECTROPORATION SYSTEMS AND CATHETERS FOR ELECTROPORATION SYSTEMS

(71) Applicant: St. Jude Medical, Cardiology Division, Inc., St. Paul, MN (US)

(72) Inventor: Israel Byrd, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 417 days.

(21) Appl. No.: 16/605,730

(22) PCT Filed: May 8, 2018

(86) PCT No.: PCT/US2018/031624
§ 371 (c)(1),
(2) Date: Oct. 16, 2019

(87) PCT Pub. No.: WO2018/208795
PCT Pub. Date: Nov. 15, 2018

(65) Prior Publication Data
US 2021/0121228 A1    Apr. 29, 2021

Related U.S. Application Data

(60) Provisional application No. 62/505,254, filed on May 12, 2017.

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00178* (2013.01);
(Continued)

(58) Field of Classification Search
CPC ............ A61B 18/1482; A61B 18/1492; A61B 2018/1435; A61B 2018/00613
See application file for complete search history.

(56) References Cited

U.S. PATENT DOCUMENTS

| 9,554,848 B2 * | 1/2017 | Stewart | A61B 18/1492 |
| 2007/0005053 A1 * | 1/2007 | Dando | A61B 18/1492 |
| | | | 606/41 |

(Continued)

OTHER PUBLICATIONS

International Search Report and Written Opinion for International Application No. PCT/US2018/031624, dated Jul. 26, 2018, 11 pages.

*Primary Examiner* — Linda C Dvorak
*Assistant Examiner* — Nicholas S Borsch
(74) *Attorney, Agent, or Firm* — Armstrong Teasdale LLP

(57) ABSTRACT

The present disclosure provides catheters for electroporation systems. One catheter includes a plurality of catheter electrodes disposed along a portion of a distal end of the electroporation catheter. The plurality of catheter electrodes includes a plurality of first type catheter electrodes adapted for use with an electroporation generator during an electroporation procedure and a plurality of second type catheter electrodes adapted for use with an electroporation generator during an electroporation procedure and for use with a diagnostic subsystem. The plurality of first type catheter electrodes is positioned at a distal end of the electroporation catheter. Each second type catheter electrode is adjacent another second type catheter electrode.

9 Claims, 7 Drawing Sheets

(52) U.S. Cl.
CPC ............... *A61B 2018/00613* (2013.01); *A61B 2018/124* (2013.01); *A61B 2018/1407* (2013.01); *A61B 2018/1467* (2013.01)

(56) References Cited

U.S. PATENT DOCUMENTS

| | | | |
|---|---|---|---|
| 2012/0059255 A1* | 3/2012 | Paul | A61B 18/14 600/431 |
| 2013/0006238 A1* | 1/2013 | Ditter | A61B 18/1492 606/41 |
| 2013/0172884 A1* | 7/2013 | Schoenbach | A61B 18/1206 606/41 |
| 2016/0143689 A1* | 5/2016 | Ditter | A61B 5/0538 600/381 |
| 2016/0256682 A1 | 9/2016 | Paul et al. | |
| 2016/0317223 A1 | 11/2016 | Avitall | |
| 2017/0035499 A1 | 2/2017 | Stewart et al. | |
| 2017/0035500 A1 | 2/2017 | Hoitink et al. | |
| 2017/0065339 A1 | 3/2017 | Mickelsen | |
| 2018/0042674 A1 | 2/2018 | Mickelsen | |
| 2018/0140347 A1* | 5/2018 | Chen | A61N 1/06 |

* cited by examiner

ELECTROPORATION SYSTEMS AND CATHETERS FOR ELECTROPORATION SYSTEMS

CROSS REFERENCE TO RELATED APPLICATIONS

This application is the national stage entry of PCT/US2018/031624, filed on May 8, 2018, which claims the benefit of priority to U.S. provisional application Ser. No. 62/505,254, filed May 12, 2017, which are incorporated herein by reference in their entirety.

A. FIELD OF THE DISCLOSURE

The present disclosure relates generally to medical devices that are used in the human body. In particular, in many embodiments, the present disclosure relates to electroporation systems, catheters for electroporation systems, and methods of controlling electroporation systems to perform both electroporation and navigation.

B. BACKGROUND

Various therapies are used to treat various conditions afflicting the human anatomy. Cardiac arrhythmias, for example are sometimes treated using ablation therapy. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric-field induced pore formation on the cell membrane. The electric field may be induced by applying a direct current (DC) signal delivered as a relatively short duration pulse which may last, for instance, from a nanosecond to several milliseconds. Such a pulse may be repeated to form a pulse train. When such an electric field is applied to tissue in an in vivo setting, the cells in the tissue are subjected to transmembrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation.

BRIEF SUMMARY OF THE DISCLOSURE

The present disclosure generally relates to electroporation systems and catheters for electroporation systems.

In one embodiment, the present disclosure is directed to a catheter having a plurality of catheter electrodes disposed along a portion of a distal end of the electroporation catheter. The plurality of catheter electrodes includes a plurality of first type catheter electrodes adapted for use with an electroporation generator during an electroporation procedure and a plurality of second type catheter electrodes adapted for use with an electroporation generator during an electroporation procedure and for use with a diagnostic subsystem. Each second type catheter electrode is adjacent another second type catheter electrode.

In another embodiment, the present disclosure is directed to an electroporation catheter including a handle located at a proximal end of the electroporation catheter, a shaft coupled to and extending from a distal end of the handle, a plurality of wires, and a distal loop subassembly coupled to a distal end of the shaft. The shaft defines an interior channel, and the plurality of wires are disposed within the interior channel. The distal loop subassembly includes a loop having a plurality of catheter electrodes disposed thereon. The plurality of catheter electrodes includes a plurality of first type catheter electrodes electrically connected to a single wire of the plurality of wires, and a plurality of second type catheter electrodes. Each second type catheter electrode is electrically connected to a different wire of the plurality of wires.

In another embodiment, the present disclosure is directed to system including a first subsystem adapted for performing a first medical procedure utilizing a catheter, a second subsystem adapted for performing a second medical procedure utilizing a catheter, a catheter, and a selection interface coupled to the first subsystem, the second subsystem, and the catheter. The catheter includes a distal loop subassembly including a loop having a plurality of catheter electrodes disposed thereon. The plurality of catheter electrodes includes a plurality of first type catheter electrodes and a plurality of second type catheter electrodes. The selection interface is configured for selectively coupling the first type catheter electrodes and the second type catheter electrodes to the first subsystem to perform the first medical procedure and for selectively coupling only the first type catheter electrodes to the second subsystem to perform the second medical procedure.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to electroporation systems and catheters for electroporation systems. The disclosed embodiments may lead to more consistent and improved patient outcomes with therapy, diagnostic, navigation, and/or mapping performed using a single catheter. It is contemplated, however, that the described features and methods of the present disclosure as described herein may be incorporated into any number of systems as would be appreciated by one of ordinary skill in the art based on the disclosure herein.

Figure 1:
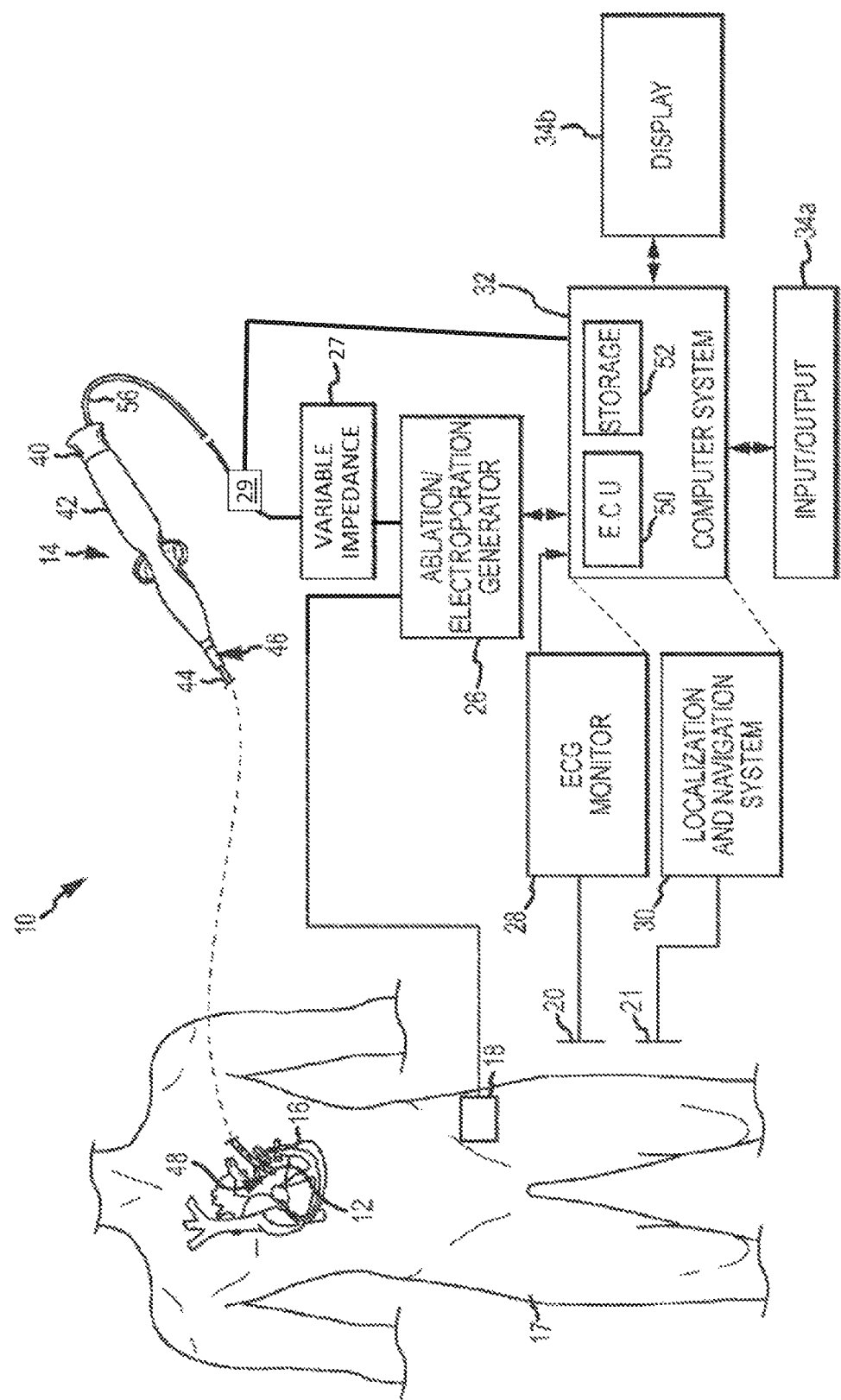
FIG. 1 is a schematic and block diagram view of a system incorporating embodiments for electroporation therapy including a variable system impedance to limit electrical arcing.

Referring now to the drawings, FIG. 1 is a diagrammatic and block diagram view of a system 10 for electroporation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient. The electrode assembly includes two types of electrode elements. The first type of electrode elements, also referred to herein as a first type catheter electrodes, are adapted for use with a first subsystem for performing a first medical procedure, such as electroporation. The first type catheter electrodes are all electrically connected together to a single connection in the catheter. The second type of electrode elements are adapted for use with the first subsystem and a second subsystem for performing a second medical procedure, such as a diagnostic, mapping, or navigation procedure. As used herein, a diagnostic procedure may include a mapping and/or navigation procedure. The second type catheter electrodes are electrically-isolated from each other within the catheter. Each second type electrode element, also referred to herein as a second type catheter electrode, is individually wired such that it can be selectively used individually or paired or combined with the first type electrode elements or any other second type electrode element to act as a bipolar or a multi-polar electrode.

System 10 may be used for irreversible electroporation to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering an electric field strength of about 0.1 to 1.0 kV/cm.

Irreversible electroporation through a multielectrode hoop catheter may enable pulmonary vein isolation in as few as one shock per vein, which may produce much shorter procedure times compared to sequentially positioning a radiofrequency (RF) ablation tip around a vein. It should be understood that the mechanism of cell destruction in electroporation is not primarily due to heating effects, but rather to cell membrane disruption through application of a high-voltage electric field. Thus, electroporation may avoid some possible thermal effects that may occur when using radio frequency (RF) energy. This "cold therapy" thus has desirable characteristics.

It should be understood that while the energization strategies are described as involving DC pulses, embodiments may use variations and remain within the spirit and scope of the invention. For example, exponentially-decaying pulses, exponentially-increasing pulses, and combinations may be used.

With this background, and now referring again to FIG. 1, system 10 includes a catheter electrode assembly 12 including at least one catheter electrode configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various sub-systems included in the overall system 10, such as an electroporation generator 26, an electrophysiology (EP) monitor such as an ECG monitor 28, a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrode may be part of electrode assembly 12 or part of a separate catheter (not shown). System 10 may further include a main computer system 32 (including an electronic control unit 50 and data storage-memory 52), which may be integrated with system 30 in certain embodiments. System 32 may further include conventional interface components, such as various user input/output mechanisms 34a and a display 34b, among other components.

Electroporation generator 26 is configured to energize the electrode element(s) in accordance with an electroporation energization strategy, which may be predetermined or may be user-selectable. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

Electroporation generator 26, sometimes also referred to herein as a DC energy source, is a monophasic electroporation generator 26 configured to generate a series DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is a monophasic defibrillator. The defibrillator is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. Electroporation generator 26 may output a DC pulse having a peak magnitude of about between about negative one kilovolt (kV) and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage. In some embodiments, the monophasic defibrillator is a Lifepak 9 defibrillator available from Physio-Control, Inc., of Redmond, Wash., USA.

A selection interface 29 allows catheter 14 to be selectively connected to electroporation generator 26 (through variable impedance 27) or to localization and navigation system 30 (through computer system 32). Moreover, selection interface 29 is operable to selectively couple different electrodes to electroporation generator or localization and navigation system 30. In the example embodiment, selection interface selectively couple a specific portion (less than all) of the electrodes to the localization and navigation system 30 during mapping, navigation, etc., and couples all of the electrodes to the electroporation generator 26 during electroporation. Other embodiments may selectively couple all electrodes or different groups of electrodes to electroporation generator or localization and navigation system 30. Selection interface 29 is discussed in more detail below with reference to FIG. 7.

A variable impedance 27 allows the impedance of the system to be varied to limit arcing from the catheter electrode of catheter 14. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26. Variable impedance 27 includes one or more impedance elements, such as resistors, capacitors, or inductors (not shown) connected in series, parallel, or combinations of series and/or parallel. In the illustrated embodiment, variable impedance 27 is connected in series with catheter 14. Alternatively, the impedance elements of variable impedance 27 may be connected in parallel with catheter 14 or in a combination of series and parallel with catheter 14. Moreover, in other embodiments, the impedance elements of variable impedance 27 are connected in series and/or parallel with return electrode 18. Some embodiments include more than one variable impedance 27, each of which may include one or more impedance elements. In such embodiments, each variable impedance 27 may be connected to a different catheter electrode or group of catheter electrodes to allow the impedance through each catheter electrode or group of catheter electrodes to be separately varied. In other embodiments, the impedance of system 10 may not need to be varied and variable impedance 27 may be omitted.

In the illustrative embodiment, the variable impedance is a variable resistance. In some embodiments variable impedance 27 includes one or more resistors (not shown) removably connected between generator 26 and catheter 14. The resistors may be connected in series, parallel, or any combination of series and parallel connections to produce a desired system impedance. Some or all of the resistors may be added, removed, or connected differently to vary the system impedance. In some other embodiments, variable impedance 27 is variable resistor, such as a rheostat or a potentiometer. In still other embodiments, variable impedance 27 includes resistors coupled together by one or more switches to allow the resistors to be selectively switched in and out of the connection between generator 26 and catheter 14. Such a variable impedance 27 may also be configured to allow some or all of the resistors to be selectively connected together in series or in parallel with each other. In some embodiments, variable impedance 27 is variable in response to an appropriate control signal from computer system 32. The resistors may be any suitable type of resistor. In all embodiments, the resistors (or other impedance elements) have relatively high energy ratings sufficient to handle the output of generator 26 without being damaged. In some embodiments, variable impedance 27 includes Ohmite PulsEater resistors available from Ohmite Mfg. Co. of Warrenville, Ill., USA. With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal 48 end. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced, retracted and/or steered or guided through body 17 to a desired location such as the site of tissue 16, including through the use of guidewires or other means known in the art.

In some embodiments, catheter 14 is a hoop catheter having catheter electrodes (not shown) distributed about one or more hoops at the distal end of shaft 44. The diameter of the hoop(s) (sometimes referred to herein as "loops") may be variable. In some embodiments, the hoop catheter diameter is variable by about ten millimeters (mm) between a minimum diameter and a maximum diameter. The minimum diameter in some embodiments may be selected between about thirteen mm and about twenty mm when the catheter 14 is manufactured. With a ten mm range of variability, such catheters would have a maximum diameter between twenty-three mm and thirty mm. In other embodiments, the hoop diameter is variable between about fifteen mm and about twenty eight mm, between about thirteen mm and about twenty-three mm, or between about seventeen mm and about twenty-seven mm. Alternatively, the catheter may be a fixed diameter hoop catheter or may be variable between different diameters. In some embodiments, catheter 14 has eight first type catheter electrodes and fourteen second type catheter electrodes grouped as seven pairs of second type catheter electrodes. In other embodiments, catheter 14 includes any other suitable number of first and second type catheter electrodes for performing electroporation. Moreover, in other embodiments, the ratio of first type catheter electrodes to second type catheter electrodes is other than 8:14. Ratios of first type catheter electrodes to second type catheter electrodes other than 8:14 may require increasing the size of the shaft of the catheter. In some embodiments, the catheter electrodes are ring electrodes, such as platinum ring electrodes. Alternatively, the catheter electrodes may be any other suitable type of electrodes, such as single sided electrode or electrodes printed on a flex material. In some embodiments, the first type catheter electrodes have lengths of 2.5 mm, and the second type catheter electrodes have lengths of about 1.3 mm. In other embodiments, the first type catheter electrodes have lengths between 2.5 mm and 3.1 mm, between 2.2 mm and 3.1 mm, or any other suitable length for use as described herein. In various embodiments, the second type catheter electrodes have lengths between 1.0 mm and 1.3 mm, between 0.9 mm and 1.5 mm, or any other suitable length for use as described herein.

The localization and navigation system 30 may be provided for visualization, mapping and navigation of internal body structures. System 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). In various embodiments, localization and navigation system 30 uses the second type catheter electrodes as bipolar pairs for visualization, mapping and navigation of internal body structures, as described in more detail below. It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

Figure 2:
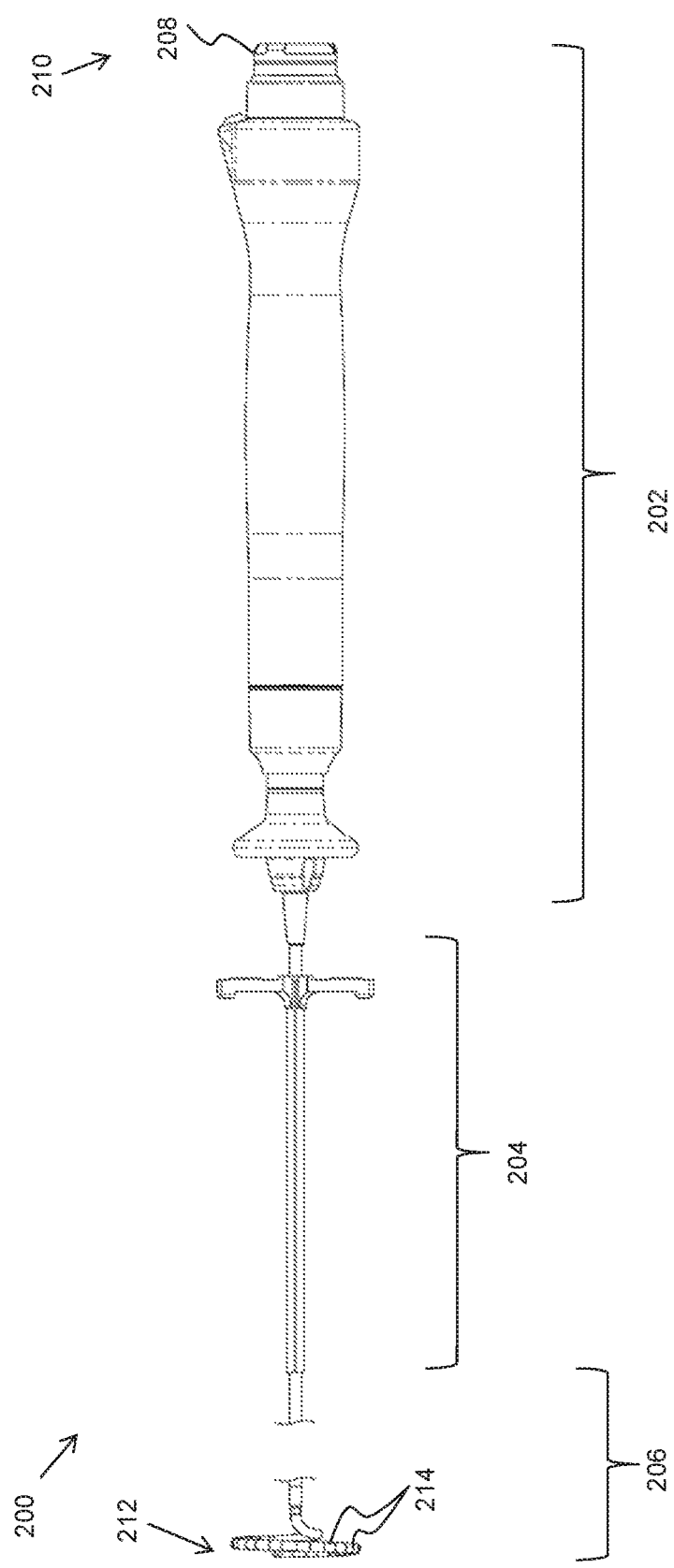
FIG. 2 is a variable diameter, multiple electrode-type catheter in an expanded configuration.

FIG. 2 is an example hoop catheter 200 usable as catheter 14 in system 10. Catheter 200 includes a handle 202, a shaft 204, a distal loop subassembly 206, and a connector 208. Hoop catheter 200 has a proximal end 210 and a distal end 212. As used herein, "proximal" refers to a direction toward the portion of the catheter 200 near the clinician, and "distal" refers to a direction away from the clinician and (generally) inside the body of a patient.

Connector 208 provides mechanical, fluid, and electrical connection(s) for cables, such as, for example, electrical cables (not shown) and/or other components of system 10 (e.g., a visualization, navigation, and/or mapping system, an ablation generator, irrigation source, etc.). Connector 208 is disposed at a proximal end 210 of hoop catheter 200, and handle 202 thereof, in particular. In the example embodiment, connector 208 is a waterproof connector. In other embodiments, connector is water resistant connector. In some embodiments, connector 208 is not itself waterproof, but includes a waterproof element to protect the connector from liquids and moisture, such as a waterproof or water resistant sheath. Connector 208 further includes an insulator or insulating material (not shown), such that connector 208 is suitable for conducting voltages in the range of one thousand volts and electrical current in the range of ten amps. In the example embodiment, connector 208 is used to couple catheter 200 to an electroporation generator, such as electroporation generator 26.

Handle 202, which is disposed at proximal end 210 of shaft 204, provides a location for the clinician to hold catheter 200 and may further provide means for steering or guiding shaft 204 within the body of the patient. Handle 202 may include means to change the length of a steering wire extending through catheter 200 to distal end 30 of shaft 204 to steer shaft 204. In other embodiments, catheter 200 may be robotically driven or controlled. Accordingly, rather than a clinician manipulating a handle to steer or guide catheter 200 and shaft 204 thereof, in such an embodiments, a robot is used to manipulate catheter 200. In various embodiments, handle 202 is a FLEXABILITY Uni-D handle with modifications configured to increase pull wire travel. Handle 202 may further include an 8F shaft lug and flush port plug. Handle 202 is at least partially hollow to define an interior channel (not shown) therethrough.

Shaft 204 is an elongate, tubular, flexible member configured for movement within body 17. In the example embodiment, shaft 204 is a size 8F shaft. Other embodiments may include a different size shaft 204. A pull wire (not shown in FIG. 2) for adjusting the diameter of the hoop and electrical conductors (not shown in FIG. 2) connected between electrodes at distal end 212 and connector 208 are disposed within an interior channel (not shown) defined by shaft 204. Shaft 204 may also permit transport, delivery, and/or removal of fluids (including irrigation fluids, cryogenic ablation fluids, and bodily fluids), medicines, and/or surgical tools or instruments. Shaft 204 may be made from conventional materials such as polyurethane, and defines one or more lumens configured to house and/or transport electrical conductors, fluids, or surgical tools. Shaft 204 may be introduced into a blood vessel or other structure within the body 17 (shown in FIG. 1) through a conventional introducer. Shaft 204 may then be steered or guided through body 17 to a desired location, such as the heart, using means well known in the art. Shaft 204 houses electrode wires (not shown in FIG. 2) for carrying electrical current to electrodes 214. Electrodes 214 include first type catheter electrodes and second type catheter electrodes (not separately identified in FIG. 2). Electrode wires extend between handle 202 and electrodes 214 within an interior portion of shaft 204. To this end, shaft 204 may include an insulator or insulating material. For example, shaft 204 may be packed with an insulation material and/or a cylindrical layer of insulation material may be circumferentially disposed within an interior portion of shaft 204. The thickness and material characteristics of such insulation are selected to configure shaft 204 for safe use with voltage and current in the range of one thousand volts and/or ten amperes.

Catheter electrodes 214 mounted on distal loop subassembly 206 may be used for a variety of diagnostic and therapeutic purposes including, for example and without limitation, electroporation, electrophysiological studies, pacing, cardiac mapping and navigation, and ablation. In a preferred embodiment, catheter electrodes 214 are configured for selective use as electroporation electrodes and navigation/mapping electrodes. For example, the first type of catheter electrodes 214 are configured for selective use for electroporation, while the second type of catheter electrodes 214 are configured for selective use for electroporation and a location or position sensing function (e.g., mapping or navigation). More particularly, the second type of catheter electrodes 214 may be selectively used as a positioning sensor(s) that provides information relating to the location (position and orientation) of catheter 200, and distal end 212 of shaft 204 thereof, in particular, at certain points in time. Accordingly, as catheter 200 is moved along a surface of a structure of interest of heart 20 (shown in FIG. 1) and/or about the interior of the structure, the sensor(s) can be used to collect location data points that correspond to the surface of, and/or other locations within, the structure of interest. These location data points can then be used by, for example, a model construction system, in the construction of a three-dimensional model of the structure of interest.

Figure 3:
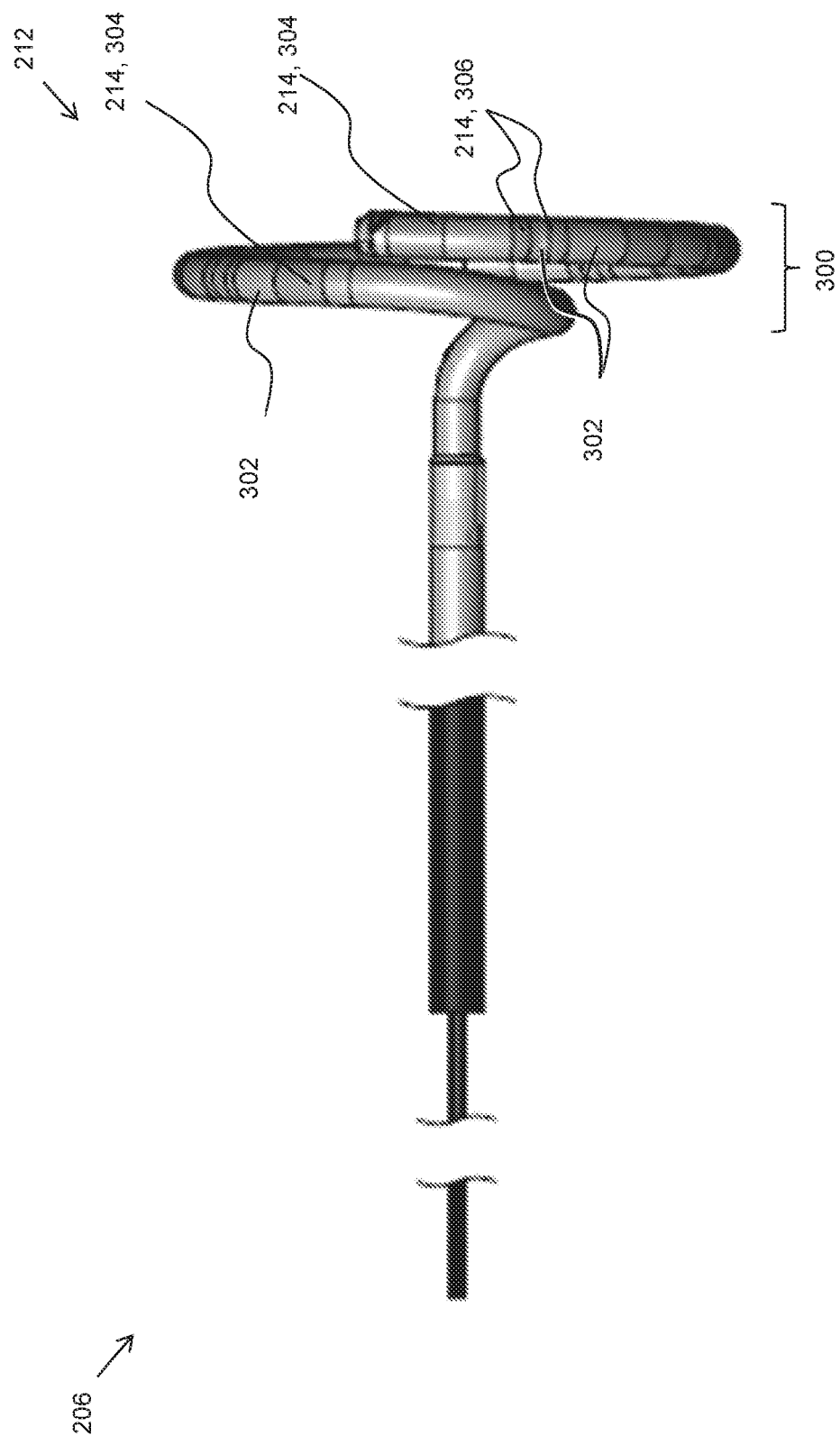
FIG. 3 is a distal loop subassembly of the hoop catheter of FIG. 2
Figure 4:
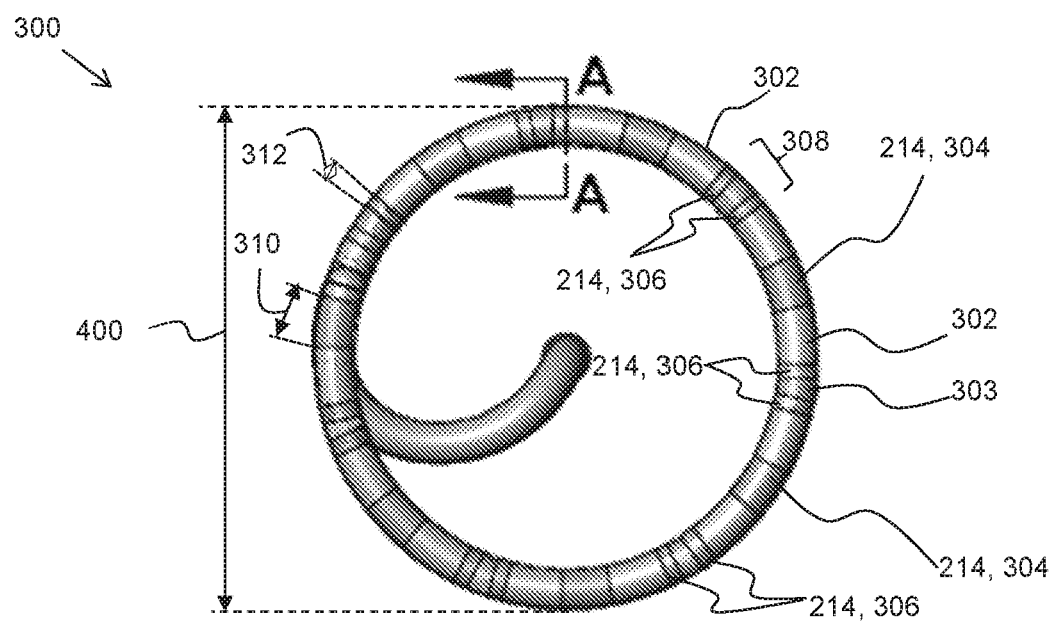
FIG. 4 is a top view of the distal loop subassembly of FIG. 3.
Figure 5:
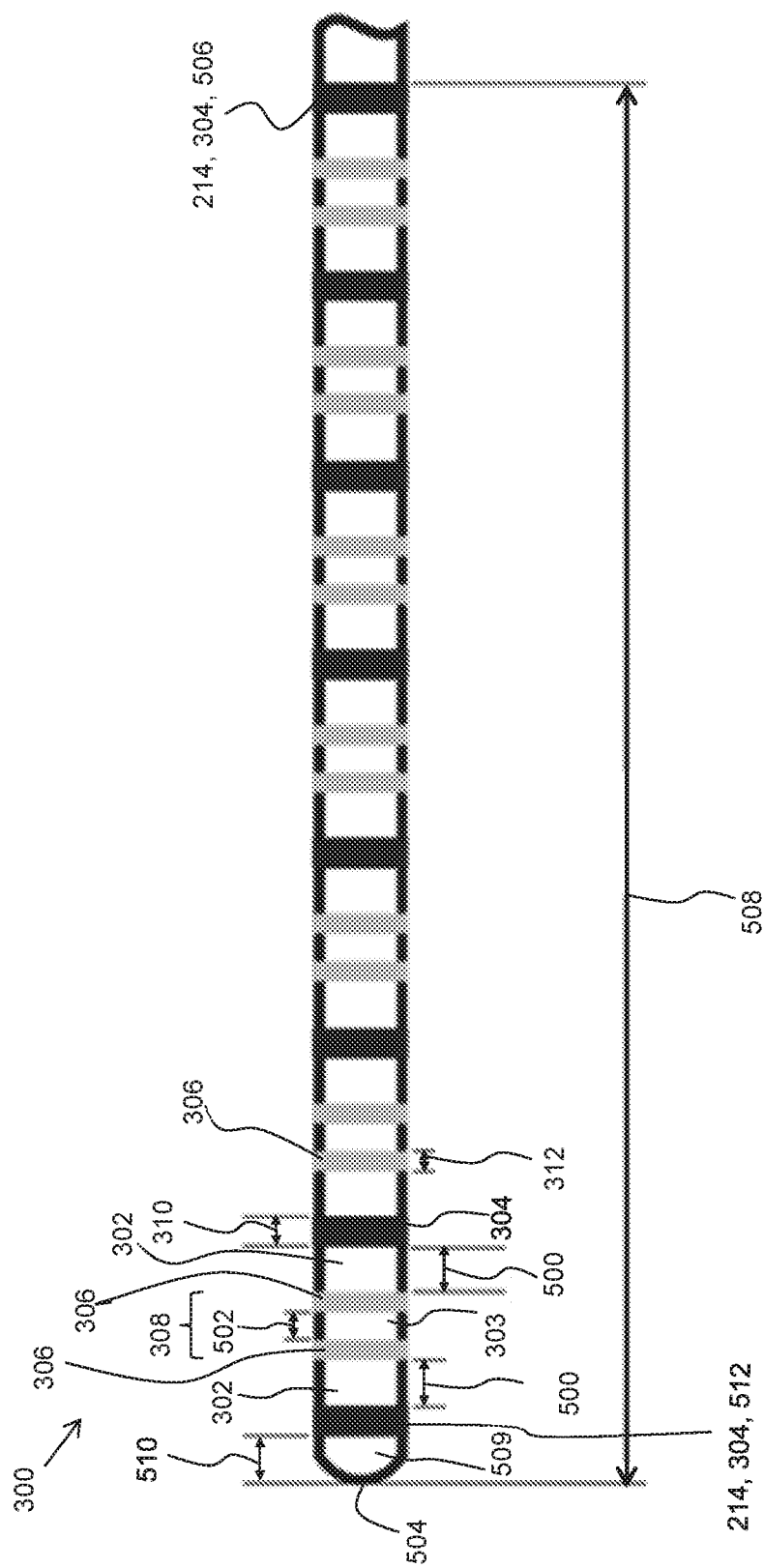
FIG. 5 is a top view of a portion of the distal loop subassembly of FIG. 3 straightened to illustrate electrode size, spacing, and configuration.

Distal loop subassembly 206 will be further described with reference to FIGS. 3, 4, and 5. FIG. 3 is a side view of distal loop subassembly 206 with a variable diameter loop 300 at distal end 212. FIG. 4 is a top view of variable diameter loop 300 of distal loop subassembly 206. FIG. 5 is loop 300 shown straightened for illustrative purposes to show electrode size, spacing, and configuration.

Variable diameter loop 300 is variable between an expanded (also referred to as "open") diameter 400 (shown in FIG. 4) and a retracted (also referred to as "closed") diameter 400 (not shown). In the example embodiment, the expanded diameter 400 is twenty seven mm and the retracted diameter 400 is fifteen mm. In other embodiments, diameter 400 may be variable between any suitable open and closed diameter 400.

Variable diameter loop 300 includes twenty-two catheter electrodes 214 spaced around the circumference of variable diameter loop 300. Catheter electrodes 214 are platinum ring electrodes configured to conduct and/or discharge electrical current in the range of one thousand volts and/or ten amperes. In other embodiments, variable diameter loop 300 may include any suitable number of catheter electrodes 214 made of any suitable material. In the example embodiment, all electrodes 214 are made of the same material. In other embodiments, one or more electrodes 214 may be made from different materials than the other catheter electrodes 214. Catheter electrodes 214 may comprise any catheter electrode suitable to conduct high voltage and/or high current (e.g., in the range of one thousand volts and/or ten amperes). Adjacent catheter electrodes 214 are separated from each other by an insulated gap 302 or 303.

Catheter electrodes 214 include first type catheter electrodes 304 and second type catheter electrodes 306. In the example embodiment, the two types of catheter electrode alternate along loop 300, with pairs of second type catheter electrodes 306 positioned adjacent a first type catheter electrodes 304. In the example embodiment, the sequence of alternating electrodes begins and ends with a first type catheter electrode and each pair of second type catheter electrodes 306 is positioned between two first type catheter electrodes 304. In other embodiments, the sequence of alternating electrodes 214 may begin or end with second type catheter electrodes 306. First type catheter electrodes 304 are separated from adjacent second type catheter electrodes 306 by an insulated gap 302 having a length 500 (shown in FIG. 5), while second type catheter electrodes 306 are separated from adjacent second type catheter electrodes 306 by insulated gaps 303 having a length 502. In the example embodiment, length 500 is 2.2 mm and length 502 is 1.5 mm. In other embodiments, lengths 500 and 502 may be any other suitable lengths. First type catheter electrodes 304 have a length 310 that is larger than a length 312 of second type catheter electrodes 306. In the example embodiment, length 310 is 2.5 mm and length 312 is 1.3 mm. In various other embodiments, length 310 is between 2.5 and 3.1 mm, between 2.2 and 3.1 mm, or any other length suitable for functioning as described herein. In various other embodiments, length 312 is between 1.0 and 1.3 mm, between 0.9 and 1.5 mm, or any other length suitable for functioning as described herein. First type catheter electrodes 304 are electrically shorted together in subassembly 212 and connect to a single wire (not shown in FIGS. 3-5) in shaft 204.

First type catheter electrodes 304 are used by system 10 during electroporation. The larger surface area of first type catheter electrodes 304, relative to second type catheter electrodes 306, is beneficial for achieving the desired current density on electrodes 214 to prevent electrical arcs from occurring during electroporation. Second type catheter electrodes 306 are shorter than first type catheter electrodes 304. Each second type catheter electrode 306 is connected to a separate wire (not shown in FIGS. 3 and 4) in shaft 204 and may be used independent of first type catheter electrodes 304 and each other second type catheter electrode 306. A selection interface (discussed in more detail below), allows second type catheter electrodes 306 to be selectively used for electroporation and navigation/mapping. During electroporation, second type catheter electrodes 306 are all shorted together and connected to first type catheter electrodes 304. During navigation/mapping, second type catheter electrodes 306 are used by localization and navigation system 30 in separate bipolar pairs 308. Each bipolar pair 308 includes two adjacent second type catheter electrodes 306 separated by an insulated gap 303 having a length 502 (shown in FIG. 5). In other embodiments, length 502 may be any other suitable length. In addition to being shorter than first type catheter electrodes 304, the second type catheter electrodes 306 in each bipolar pair 308 are separated from each other by an insulated gap 303 that is shorter than the insulated gaps 302 separating the bipolar pair 308 from adjacent first type catheter electrodes 304. Generally, shorter electrodes with closer spacing between them perform better with electrogram signals that may be used for diagnostic/mapping/navigation procedures. In the example embodiment, each first type catheter electrode 304 is the same length 310 as each other first type catheter electrode 304, and each second type catheter electrode 306 is the same length 312 as each other second type catheter electrode 306. The insulated gaps 302 are all the same size as each other (i.e., have the same length 500), and insulated gaps 303 are all the same size as each other (i.e., have the same length 502). Insulated gaps 302 are not the same size as insulated gaps 303. In other embodiments, insulated gaps 302 and 303 may have the same size, one or more insulated gaps 302 may be different sizes from other insulated gaps 302, and/or one or more insulated gaps 303 may be different sizes from other insulated gaps 303.

Diameter 400 and catheter electrode 214 spacing may be developed to provide a targeted range of energy density to tissue, as well as to provide sufficient electroporation coverage for different human anatomic geometries. In general, a sufficient number of electrodes 214 with appropriate lengths 310 and 312 are desired to provide substantially even and continuous coverage around the circumference of variable diameter loop 300, while still allowing enough flexibility to allow variable diameter loop 300 to expand and contract to vary diameter 400 to the desired extremes. As mentioned above, length 310 of first type catheter electrodes 304 may be varied. Increasing length 310 of first type catheter electrodes 304 may increase coverage of electrodes 214 around the circumference of loop 300 while also decreasing current density (by increasing the surface area) on electrodes 214, which may help prevent arcing during electroporation operations. Increasing length 310 too much, however, may prevent variable diameter loop 300 from forming a smooth circular shape and may limit the closed diameter 400 of variable diameter loop 300. Additionally, too great a length 310 may increase the surface area of catheter electrodes 214 to a point that the current density applied to catheter electrodes 214 by a power source is below the minimum current density needed for successful therapy. Conversely, decreasing length 310 decreases the surface area, thereby increasing the current density (assuming no other system changes) on catheter electrodes 214. As discussed above, greater current densities may lead to increased risk of arcing during electroporation, and may result in larger additional system resistances needing to be added to prevent electroporation. Moreover, in order to get a desired, even coverage about the circumference of variable diameter loop 300, more catheter electrodes 214 may be needed if length 310 is decreased. Increasing the number of catheter electrodes 214, whether first type catheter electrodes 304 or second type catheter electrodes 306, on variable diameter loop 300 may prevent variable diameter loop 300 from being able to be contracted to a desired minimum diameter 400 and/or may require more wires than can fit in a desired size of shaft 204. Similarly, increasing length 312 of second type catheter electrodes 306 may increase coverage of electrodes 214 around the circumference of loop 300 while also decreasing current density (by increasing the surface area) on electrodes 214, which may help prevent arcing during electroporation operations. However, increasing length 312 may also decrease mapping/navigation performance of catheter 200. Conversely, decreasing length 312 decreases the surface area of electrode 214, thereby increasing the current density (assuming no other system changes) on catheter electrodes 214.

By selectively using a combination of first type catheter electrodes 304 and second type catheter electrodes 306, catheter 200 can be used for electroporation and navigation/mapping without increasing the size of shaft 204. As discussed above, for navigation and mapping, electrodes 214 are each separately connected to localization and navigation system 30. Thus, if all electrodes 214 were used for navigation and mapping, twenty-two wires would need to extend through shaft 204 in the example embodiment. Twenty-two wires of sufficient size to carry the voltage and current used in electroporation will not fit in a size 8F shaft. A larger shaft could be used, with potential added patient discomfort, difficulty of maneuvering into position, and possible safety concerns. Moreover, if too large a shaft were needed to house all of the wires, shaft 204 may simply be too large to fit in portions of the patient's body 17. Using fewer electrodes 214 would reduce the number of wires, but may decrease performance of catheter 200. Decreasing the number of electrodes 214 may require increased spacing between electrodes 214, leading to potential gaps in applied therapy and poorer performance for navigation and mapping. Also, as discussed above, decreasing the number of electrodes 214 would require increased electrode size to maintain the same surface area, which can lead to reduced flexibility and poorer navigation and mapping performance.

As seen in FIG. 5, the portion of loop 300 from an end 504 of loop 300 to a last first type catheter electrode 506 has a length 508. In the example embodiment, length 508 is 81.55 mm. An insulated gap 509 extends a distance 510 between end 504 and a first type catheter electrode 512. In the example embodiment, distance 510 is 2.0 mm. In other embodiments, length 508 and distance 510 may be any other suitable length or distance.

Figure 6:
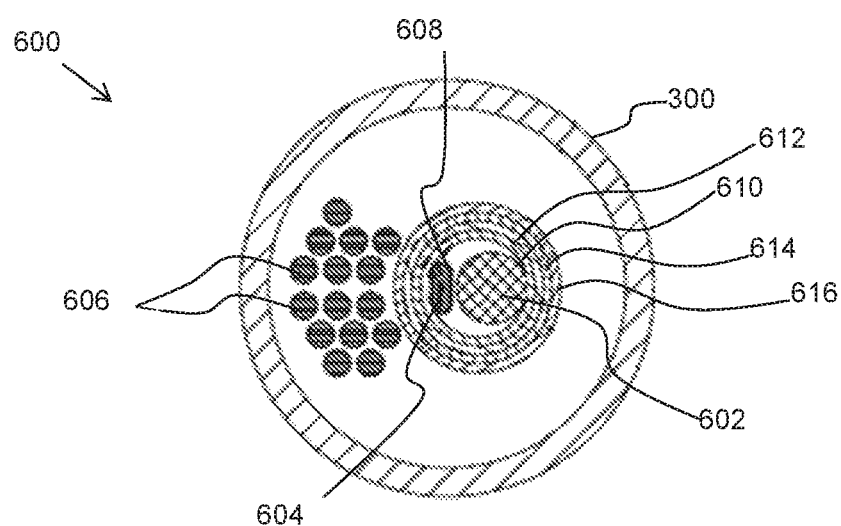
FIG. 6 is a cross-sectional view of a portion of the distal loop subassembly of FIG. 4 taken along the lone A-A.

FIG. 6 is a cross-section 600 of variable diameter loop 300 taken along the line A-A shown in FIG. 4. Cross-section 600 includes a shape memory wire 602, a pull wire 604, electrode wires 606, and tubing 608, 610, 612, 614, and 616.

Shape memory wire 602 is pre-shaped to a loop configuration at a particular diameter 400 to shape variable diameter loop 300 into its circular shape of the expanded diameter 400. After a change in shape of variable diameter loop 300, such as a change in diameter 400 or a straightening for insertion into a patient's body, shape memory wire 602 will substantially return variable diameter loop 300 to its initial shape and diameter 400. In the example embodiment, shape memory wire 602 is a nitinol wire. In other embodiments, shape memory wire 602 may be any other suitable shape memory alloy.

Pull wire 604 is configured to permit an operator to vary diameter 400 of variable diameter loop 300 by moving a proximal end (not shown) of pull wire 604 toward or away from proximal end 210. Pull wire 604 is surrounded by tubing 608. Tubing 608 is a polyethylene terephthalate (PET) shrink tubing. In other embodiments, tubing 608 may be any other suitable tubing for insulating and protecting pull wire 604.

Electrode wires 606 carry electrical current from a power source coupled to connector 208 to catheter electrodes 214. Electrode wires 606 are any suitable size and material sufficient to carry the voltage and current required for electroporation, as described herein. In the example embodiment, there are fifteen electrode wires. One electrode wire 606 is connected to all of first type catheter electrodes 304. The remaining fourteen electrode wires 606 are each connected to a different second type catheter electrode 306. Electrode wires 606 are isolated from one another and are not electrically connected to each other within catheter 200.

Shape memory wire 602 and pull wire 604 are separated from and electrically insulated from electrode wires 606 by tubing 610, 612, 614, and 616. In the example embodiment, tubing 610 is a polytetrafluoroethylene (PTFE) tubing, tubing 612 is a polyimide tubing, and tubing 614 and 616 are PET shrink tubing.

Hoop catheter 200 may further incorporate additional insulation materials to accommodate high voltages and currents. For instance, hoop catheter 200 may include an insulator, such as wire sheathing (not shown), that surrounds each electrode wire 606. Such a wire sheathing may, for example, have a thickness of 0.0015 inches. Similarly, hoop catheter 200 may include insulation material (not shown) that is packed or bundled around electrode wires 606 to insulate electrode wires 606 from one another and/or from other components of hoop catheter 200.

Figure 7:
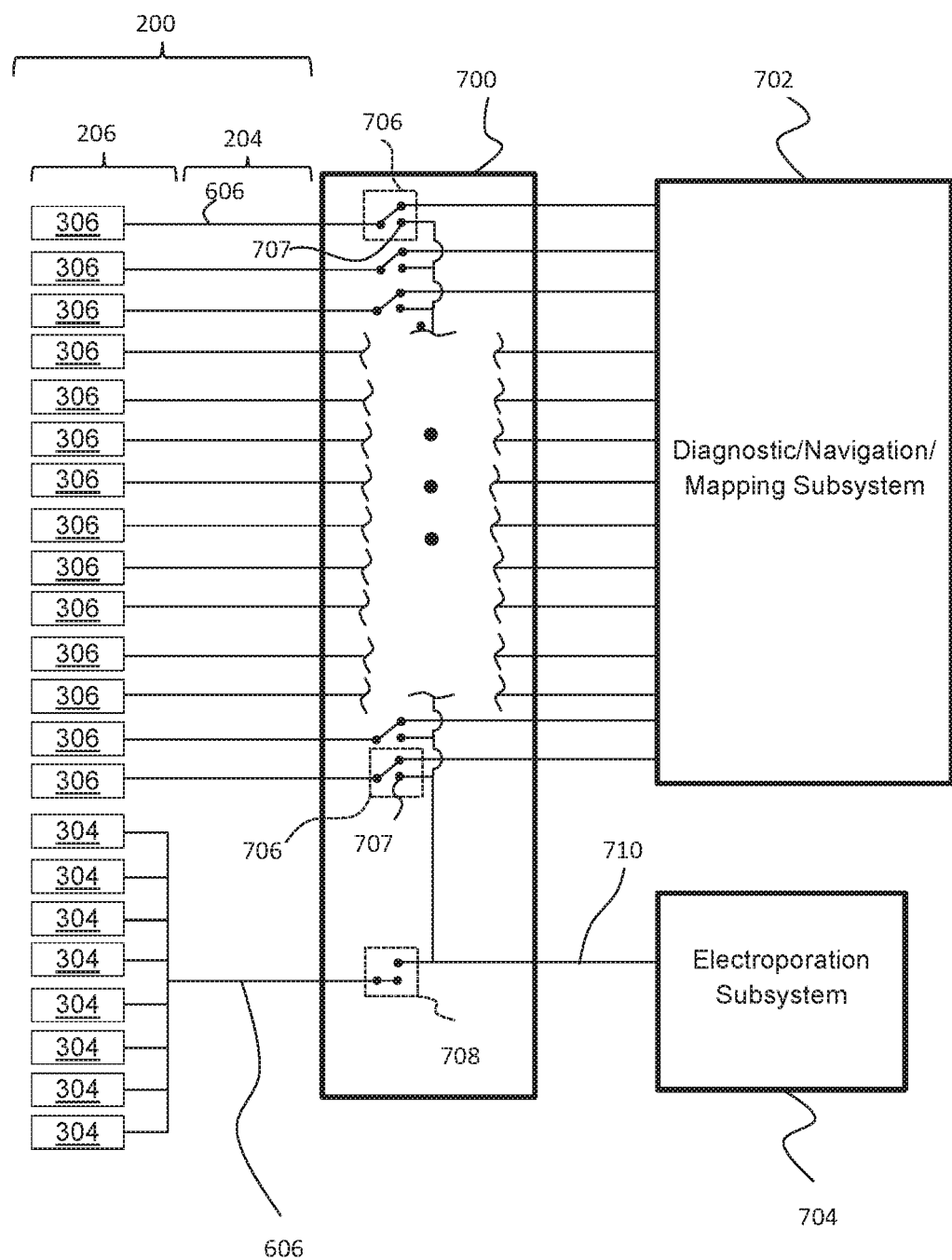
FIG. 7 is a block diagram of an example diagnostic and treatment system using a single catheter for mapping/diagnostic procedures and electroporation.

FIG. 7 is a block diagram of an example selection interface 700 that may be used as selection interface 29. Selection interface 700 is connected between catheter 200 and a diagnostic/navigation/mapping subsystem 702 and an electroporation subsystem 704. Diagnostic/diagnostic/navigation/mapping subsystem 702 may include, for example, computer system 32 and localization and navigation system 30. Electroporation subsystem 704 may include, for example, variable impedance 27 and electroporation generator 26. In other embodiments, diagnostic/navigation/mapping subsystem 702 and an electroporation subsystem 704 may be any two suitable subsystems for use with catheter 200.

Selection interface 700 is operable to select which of electroporation subsystem 704 and diagnostic/navigation/mapping subsystem 702 is coupled to catheter 200, and more specifically, the first and second type catheter electrodes 304, 306. Thus, for example, an operator of system 10 may insert the appropriate portion of catheter 200 into a patient while coupled by selection interface 700 to diagnostic/navigation/mapping subsystem 702 to navigate catheter to a desired electroporation site and/or to map a portion of the patient. Once the catheter is suitably positioned, the same catheter 200 may be coupled by selection interface 700 to electroporation subsystem 704 by the operator making such a selection using selection interface 700, and electroporation may proceed as described herein.

Selection interface 700 includes a plurality of switches 706 coupled via electrode wires 606 to second type cathode electrodes 306. A switch 708 is coupled via electrode wires 606 to first type cathode electrodes 304. When connection to diagnostic/navigation/mapping subsystem 702 is selected, switches 706 and 708 are switched as shown in FIG. 7. All second type catheter electrodes 306 are separately coupled through switches 706 to diagnostic/navigation/mapping subsystem 702, and all first type catheter electrodes 304 are left unconnected to either subsystem 702 or 704. In the example embodiment, first type catheter electrodes 304 are left in an open circuit by switch 706. In other embodiments, first type catheter electrodes 304 are grounded by switch 706 when diagnostic/navigation/mapping subsystem 702 is selected. When connection to electroporation subsystem 704 is selected, switches 706 switch to connect wires 606 to their node 707. Thus, all electrodes 306 are connected in to a single wire 710. Switch 708 also changes its state and couples all of first type catheter electrodes 304 to wire 710. Wire 710 is connected to electroporation subsystem 704 and couples electrodes 304 and 306 to electroporation subsystem 704. In other embodiments first type catheter electrodes may be coupled to electroporation subsystem 704 through a separate wire from second type catheter electrode. In other embodiments, other electrical configurations and combinations of electrical configurations may be used. In various embodiments, selection of the desired connectivity may be made manually on selection interface 700 or in a user interface of computer system 32. Alternatively, or additionally, selection of the desired connectivity may be made automatically, such as by computer system 32 in response to a user selection to start a navigation, mapping, or electroporation procedure using computer system. In some embodiments, selection interface may be included within catheter 200 or within one or more other components of system 10, such as within computer system 32.

Selection interface 700 facilitates selection of which catheter electrodes 214 are coupled to the selected electroporation subsystem 704 or diagnostic/navigation/mapping subsystem 702, and in what electrical configuration. Switching between electrodes 214 and electrical configuration of electrodes may be accomplished by any suitable mechanical, electrical or electro-mechanical switches 704, 706 within selection interface 700.

Although the above embodiments are described in association with a hoop catheter, those of skill in the art will appreciate that the systems and methods described herein may also be implemented using a basket catheter including a plurality of splines. In such embodiments, each spline would include a plurality of electrodes in an arrangement similar to the electrode arrangement described for variable diameter loop 300 (shown in FIGS. 3-6). For example, for an N-spline basket catheter, the electrodes may be arranged as indicated in the following Table 1 (with each column representing a spline):

TABLE 1

| 1 | 2 | ... | N-1 | N |
| --- | --- | --- | --- | --- |
| E1 | E2 | ... | E1 | E2 |
| E2 | E2 | ... | E2 | E2 |
| E2 | E1 | ... | E2 | E1 |
| E1 | E2 | ... | E1 | E2 |
| E2 | E2 | ... | E2 | E2 |
| E2 | E1 | ... | E2 | E1 |

In Table 1, E1 indicates an electrode is the first type catheter electrode and E2 indicates an electrode is the second type catheter electrode. As in the embodiments described for variable diameter loop 300, the second type catheter electrodes are grouped in pairs. Further, as shown in Table 1, the pattern of the first and second type catheter electrodes alternates between splines. Alternatively, each spline may have the same pattern.

For the basket catheter, the first type catheter electrodes may have a length of approximately 2.2 mm, and the second type catheter electrodes may have a length of approximately 1.5 mm. Alternatively, the first type catheter electrodes and the second type catheter electrodes may have any suitable length. Further, although Table 1 indicates each spline includes six electrodes, in other embodiments, each spline may include any suitable number of electrodes. For example, because the first type catheter electrodes are all electrically connected together, additional first type catheter electrodes may be included, as no additional wires need to be added for those electrodes.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electroporation catheter comprising:
   a plurality of catheter electrodes disposed along a portion of a distal end of the electroporation catheter, the plurality of catheter electrodes comprising:
      a plurality of first type catheter electrodes adapted for use with an electroporation generator during an electroporation procedure; and
      a plurality of second type catheter electrodes adapted for use with the electroporation generator during the electroporation procedure and for use with a diagnostic subsystem, wherein each second type catheter electrode is adjacent another second type catheter electrode, and wherein both the first type catheter electrodes and the second type catheter electrodes are selectively couplable to the electroporation generator to deliver energy as part of the electroporation procedure;
   a first wire connected to all of the plurality of first type catheter electrodes; and
   a plurality of second wires, each second wire of the plurality of second wires connected to an associated one of the plurality of second type catheter electrodes, wherein, to perform the electroporation procedure, the second type catheter electrodes are selectively couplable to the first type catheter electrodes using switching circuitry connected to the first wire and the plurality of second wires.

2. The electroporation catheter of claim 1, wherein adjacent second type catheter electrodes form a pair of second type catheter electrodes, and the first type catheter electrodes and pairs of second type catheter electrodes are alternately positioned along the portion of the electroporation catheter with every first type catheter electrode adjacent at least one pair of second type catheter electrodes.

3. The electroporation catheter of claim 2, wherein each pair of second type catheter electrodes is positioned between two first type catheter electrodes.

4. The electroporation catheter of claim 1, wherein each first type catheter electrode has a first length, each second type catheter electrode has a second length, and the first length is different than the second length.

5. The electroporation catheter of claim 4, wherein the first length is 2.5 millimeters (mm), and the second length is 1.3 mm.

6. The electroporation catheter of claim 1, further comprising a plurality of insulation gaps, each insulation gap positioned between adjacent catheter electrodes.

7. The electroporation catheter of claim 6, wherein the insulation gap between adjacent first and second type catheter electrodes has a first length, the insulation gap between adjacent second type catheter electrodes has a second length, and the first length is different than the second length.

8. The electroporation catheter of claim 7, wherein the first length is 2.2 millimeters (mm), and the second length is 1.5 mm.

9. The electroporation catheter of claim 1, wherein the portion of the distal end of the electroporation catheter comprises a variable diameter loop.

* * * * *